(12) United States Patent
Crucs (10) Patent No.: US 8,447,378 B2
(45) Date of Patent: May 21, 2013

(54) SYSTEM AND METHOD OF CAPTURING IMAGES

(75) Inventor: Kevin M. Crucs, Akron, OH (US)

(73) Assignee: Apteryx, Inc., Akron, OH (US)

( * ) Notice: Subject to any disclaimer, the term of this patent is extended or adjusted under 35 U.S.C. 154(b) by 2826 days.

(21) Appl. No.: 11/078,810

(22) Filed: Mar. 11, 2005

(65) Prior Publication Data
US 2006/0239521 A1   Oct. 26, 2006

(51) Int. Cl.
*A61B 5/05*    (2006.01)
*A61B 6/14*    (2006.01)

(52) U.S. Cl.
USPC ............................................. 600/407; 378/38

(58) Field of Classification Search
USPC ............. 600/407; 378/38, 98.2, 99, 162–166; 358/111; 382/128, 132, 232; 433/2, 24, 213–215; 705/2, 3
See application file for complete search history.

(56) References Cited

U.S. PATENT DOCUMENTS

| | | | | |
|---|---|---|---|---|
| 3,849,596 A * | 11/1974 | Lawrence | | 348/564 |
| 4,941,164 A * | 7/1990 | Schuller et al. | | 378/205 |
| 5,179,579 A * | 1/1993 | Dove et al. | | 378/38 |
| 5,381,457 A * | 1/1995 | Burns | | 378/166 |
| 5,572,566 A * | 11/1996 | Suzuki et al. | | 378/98.2 |
| 7,286,954 B2 * | 10/2007 | Kopelman et al. | | 702/152 |
| 2003/0065523 A1 * | 4/2003 | Pruche et al. | | 705/1 |

* cited by examiner

*Primary Examiner* — Long V. Le
*Assistant Examiner* — Bradley Impink
(74) *Attorney, Agent, or Firm* — Hahn Loeser & Parks LLP (57) ABSTRACT

A system and methods for capturing, displaying, and viewing representations of progressions of anatomical structures and associated digital images is disclosed. A processor-based system is used to generate and store digital images of anatomical structures such as teeth of a dental patient. Any one digital image is stored as an image shot within a progression of image shots. The progression of image shots may correspond to a particular region of interest or study being performed by a dental practitioner. The progression of image shots is depicted to the practitioner as a tooth progression chart including pictorial representations of the anatomical structures, in correct anatomical relation to each other, and indicia defining an ordered progression such that the practitioner is able to clearly identify which anatomical structure is associated with a particular image shot.

30 Claims, 10 Drawing Sheets

SYSTEM AND METHOD OF CAPTURING IMAGES

TECHNICAL FIELD

Certain embodiments of the present invention relate to digital imaging. More particularly, certain embodiments of the present invention relate to a system and methods for capturing, displaying, and viewing representations of progressions of anatomical structures and associated digital images.

BACKGROUND OF THE INVENTION

Due to the latest shift in paradigms, more and more doctors are shifting to an "exam" or "study" based approach to patient care. The concept of a study in these paradigms moves away from a smearing of image acquisitions to more of a specific region-of-interest (ROI) approach. In dentistry, for example, while the concept of a full-mouth series (FMX) of images still has its place in this paradigm, the FMX changes from the primary diagnosis tool to more of a historical milestone that can be used as a historical frame of reference for a current ROI. When a doctor needs to reference a ROI for a current study, he is typically only interested in historical images that reference the current ROI for the current study. In other words, the doctor typically only wants to reference the images that directly pertain to the current ROI. In addition, with refinements, advancements and quality increases in digital pantomograph X-ray systems, pantomograph X-rays are quickly replacing FMXs as the preferred method for taking complete mouth X-rays. Pantomograph images can be taken more quickly and require far less hassle in terms of interaction time and sterilization. This shift to pantomograph systems results in intra-oral X-rays being used for specific ROI images.

While mounted series proved invaluable in organizing historical hard copies of images in file folders, their use in today's digital world is more legacy than practical. Once the doctor viewed the images in the new template, these templates were stored in the patient's chart only to remain there until the doctor may one day want to look at the historical progression of a particular area in a patient's mouth. Since these images were physical hard copies, the doctor knew where to look in each of the templates for the ROI. Today, electronic organization of images means that doctors no longer have to sift through template after template looking for specific images that they are interested in for a ROI. Templates are typically graphically represented by boxes positioned in anatomical positions.

U.S. Pat. No. 5,179,579 to Dove et al. describes a method and apparatus for storing and displaying radiographs, particularly intra-oral radiographs. When processing intra-oral radiographs, an icon takes the form of a dental film holder, with the positions of the film holder corresponding to anatomical sites readily recognized by dentists, each position of the film holder being arranged in anatomical relation to other positions of the film holder icon.

Further limitations and disadvantages of conventional, traditional, and proposed approaches will become apparent to one of skill in the art, through comparison of such systems and methods with the present invention as set forth in the remainder of the present application with reference to the drawings.

BRIEF SUMMARY OF THE INVENTION

A first embodiment of the present invention provides a method of graphically representing a sequence of anatomical structures to be imaged or which have been imaged. The method comprises displaying a pictorial representation of at least two anatomical structures such that the at least two anatomical structures are positioned in correct anatomical relation to each other in the pictorial representation. The method further comprises displaying at least one indicia for each of the at least two anatomical structures as a part of the pictorial representation such that it is apparent which indicia are associated with which anatomical structures. Also, the indicia define an ordered progression in which the at least two anatomical structures are to be imaged or have been imaged.

Another embodiment of the present invention comprises a method of capturing a sequence of anatomical images using a computer-based platform. The method includes displaying a pictorial representation of at least two anatomical structures to be imaged on a display of the computer-based platform such that the at least two anatomical structures are positioned in correct anatomical relation to each other in the pictorial representation. The method further includes displaying at least one indicia for each of the at least two anatomical structures as a part of the pictorial representation on the display of the computer-based platform such that it is apparent which indicia are associated with which anatomical structures. Also, the indicia define an ordered progression in which images of the at least two anatomical structures are to be acquired from a patient. The method further includes positioning a first imaging device of the computer-based platform with respect to a first anatomical structure of the patient and corresponding to a first anatomical structure of the pictorially represented anatomical structures. The method also includes acquiring a first image of the first anatomical structure of the patient using the first imaging device and displaying the first image within a corresponding first image layout on the display of the computer-based platform. The method further includes repositioning the first imaging device, or positioning a second imaging device, with respect to a second anatomical structure of the patient and corresponding to a second anatomical structure of the pictorially represented anatomical structures. The method also includes acquiring a second image of the second anatomical structure of the patient using the first imaging device, or the second imaging device, and displaying the second image within a corresponding second image layout on the display of the computer-based platform.

A further embodiment of the present invention comprises a method of viewing a sequence of previously captured anatomical images on a computer-based platform. The method comprises displaying a pictorial representation of at least two anatomical structures to be viewed on a display of the computer-based platform such that the at least two anatomical structures are positioned in correct anatomical relation to each other in the pictorial representation. The method further comprises displaying at least one indicia for each of the at least two anatomical structures as a part of the pictorial representation on the display of the computer-based platform such that it is apparent which indicia are associated with which anatomical structures. Also, the indicia define an ordered progression in which images associated with the at least two anatomical structures have been previously acquired from a patient using at least one imaging device. The method also includes displaying one image layout for each anatomical structure for which the images have been previously acquired on the display of the computer-based platform such that it is apparent which anatomical structure is associated with which image layout. The method further comprises displaying one previously acquired image within each image layout on the display of the computer-based platform such that each displayed image corresponds to the anatomical structure associated with each image layout.

Another embodiment of the present invention comprises a computer-based system for capturing and displaying progressions of anatomical images. The system comprises a display and a means for generating and displaying, on the display, a pictorial representation of at least two anatomical structures to be imaged and associated indicia such that the at least two anatomical structures are positioned in correct anatomical relation to each other in the pictorial representation. Also, the associated indicia define an ordered progression in which images of the at least two anatomical structures are to be acquired or have been acquired from a patient. The system further comprises at least one imaging device for generating at least two digital images of the at least two anatomical structures of the patient corresponding to the displayed pictorial representation of the at least two anatomical structures. The system also comprises a memory to store the at least two digital images. The system further comprises a means for generating and displaying, on the display, one image layout for each of the at least two digital images such that it is apparent which anatomical structure is associated with which image layout. The at least two digital images are displayed within the image layouts on the display in proper correspondence to the at least two anatomical structures.

These and other advantages and novel features of the present invention, as well as details of an illustrated embodiment thereof, will be more fully understood from the following description and drawings.

DETAILED DESCRIPTION OF THE INVENTION

Figure 1:
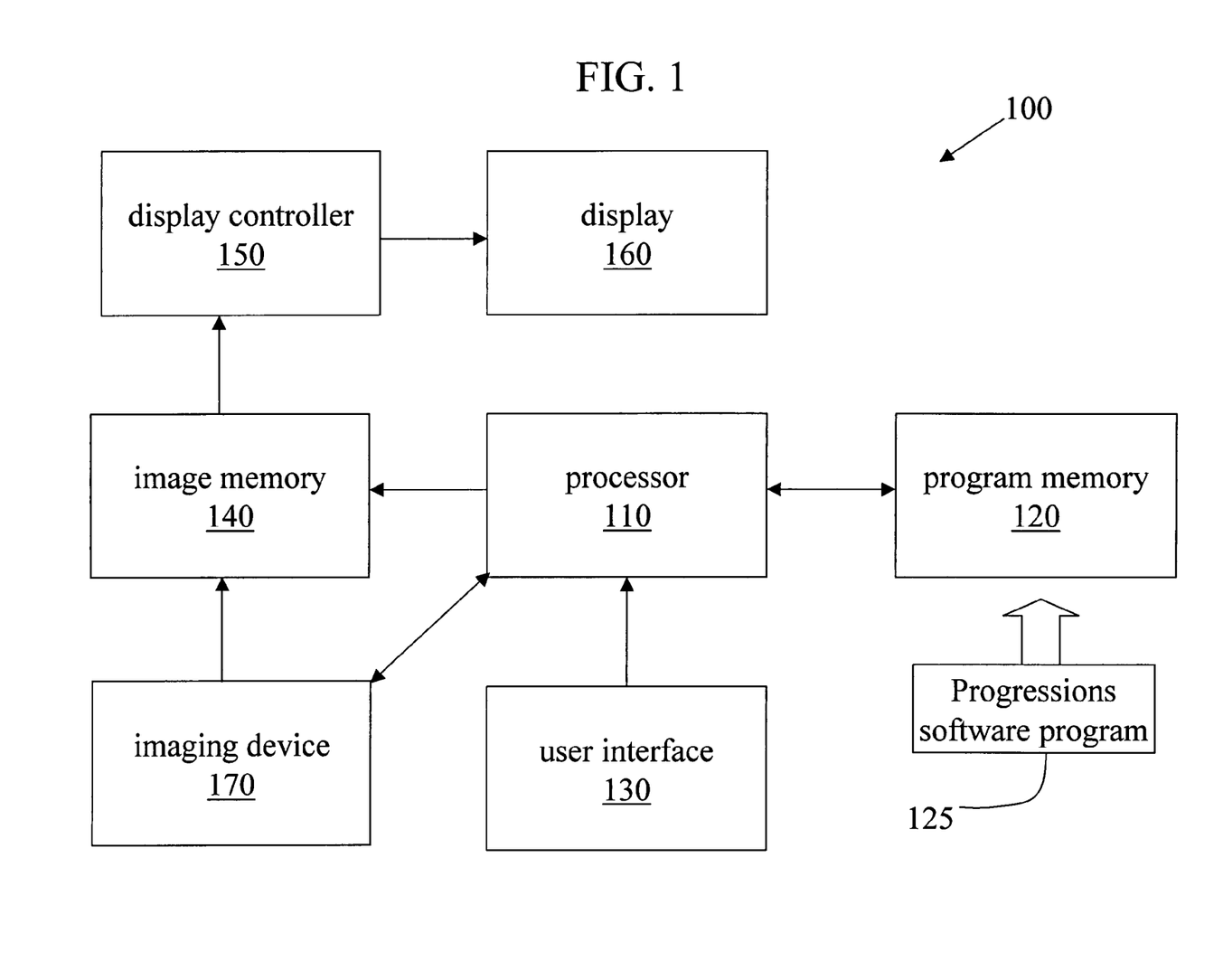
FIG. 1 is a schematic block diagram of an exemplary embodiment of a computer-based system for capturing and displaying progressions of anatomical images, in accordance with various aspects of the present invention.

FIG. 1 is a schematic block diagram of an exemplary embodiment of a computer-based system 100 (e.g., a PC-based platform) for capturing and displaying progressions of anatomical images, in accordance with various aspects of the present invention. The system 100 comprises a processor 110, a program memory 120 storing a progressions software program 125, a user interface 130, an image memory 140, a display controller 150, a display 160, and an imaging device 170.

The processor 110 interfaces to the program memory 120 and executes the progressions software program 125. The user interface 130 connects to the processor 110 to allow a user of the system 100 to select and control various functions of the system 100. The image memory 140 interfaces to the processor 110 to store image data to be displayed. The display controller 150 interfaces to the image memory 140 to extract image data from the image memory in a controlled manner and convert the image data to video data. The display 160 interfaces to the display controller 150 to accept video data from the display controller 150 such that the video data is presented to a user on the display 160. The imaging device 170 interfaces to the processor 110 and the image memory 170.

The progressions software program 125 is the executable program to run the system 100. The user interface 130 may comprise, for example, a keyboard, a mouse, a touch-screen (i.e., the user interface 130 is combined with the display 160), or push buttons. The functionality controlled through the user interface 130 includes, for example, selecting a progression of image shots, selecting an individual image shot, and capturing a digital image.

As an example, a user (e.g., a dentist) may want to take an image of a tooth of a patient using the system 100. The dentist aligns the imaging device 170 (e.g., a digital X-ray device) with a tooth of the patient and presses a button on the user interface 130 to administer an X-ray dose from the device 170 and capture a resultant digital image (i.e., image shot) of the tooth in the image memory 140. In accordance with an embodiment of the present invention, the captured digital image is stored in the image memory 140 as a designated image shot of a predefined progression of image shots for the patient. For example, the progression of image shots may correspond to a bite wing series of the patient. The dentist may continue in a similar manner to complete the capturing of a plurality of image shots to complete the bite wing series progression.

In accordance with various embodiments of the present invention, the imaging device 170 may comprise any digital imaging device including any one of, for example, an intra-oral digital X-ray device, an intra-oral digital camera, and an intra-oral digital video camera. Other imaging devices are possible as well for imaging teeth or other types of anatomy (e.g., an MRI imaging device, a luminescence imaging device, an electrical potential imaging device).

Figure 2:
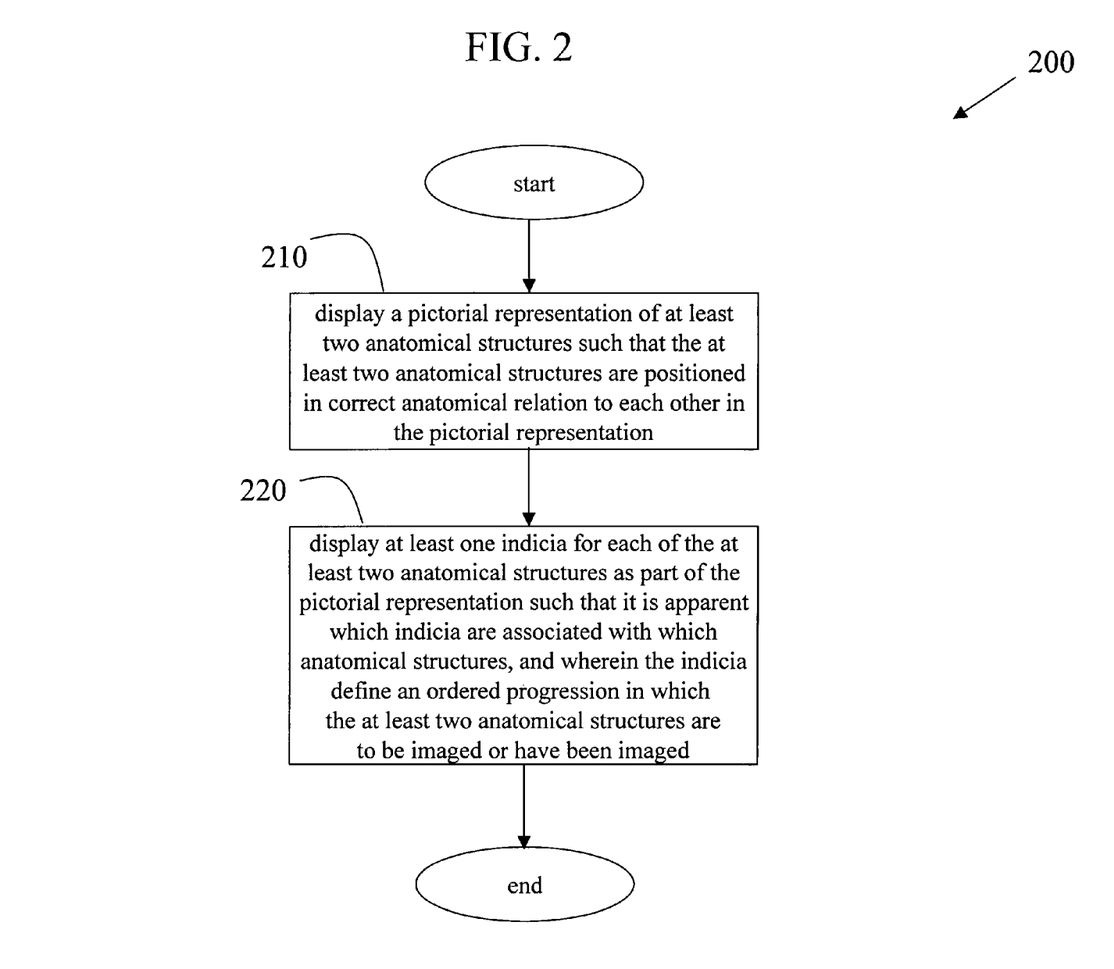
FIG. 2 is a flowchart of an embodiment of a method of graphically representing a sequence of anatomical structures to be imaged or which have been imaged using the system of FIG. 1, in accordance with various aspects of the present invention.

FIG. 2 is a flowchart of an embodiment of a method 200 of graphically representing a sequence of anatomical structures to be imaged or which have been imaged using the system 100 of FIG. 1, in accordance with various aspects of the present invention. In step 210, a pictorial representation of at least two anatomical structures is displayed such that the at least two anatomical structures are positioned in correct anatomical relation to each other in the pictorial representation. In step 220, at least one indicia is displayed for each of the at least two anatomical structures as a part of the pictorial representation such that it is apparent which indicia are associated with which anatomical structures. Also, the indicia define an ordered progression in which the at least two anatomical structures are to be imaged or have been imaged.

Figure 3:
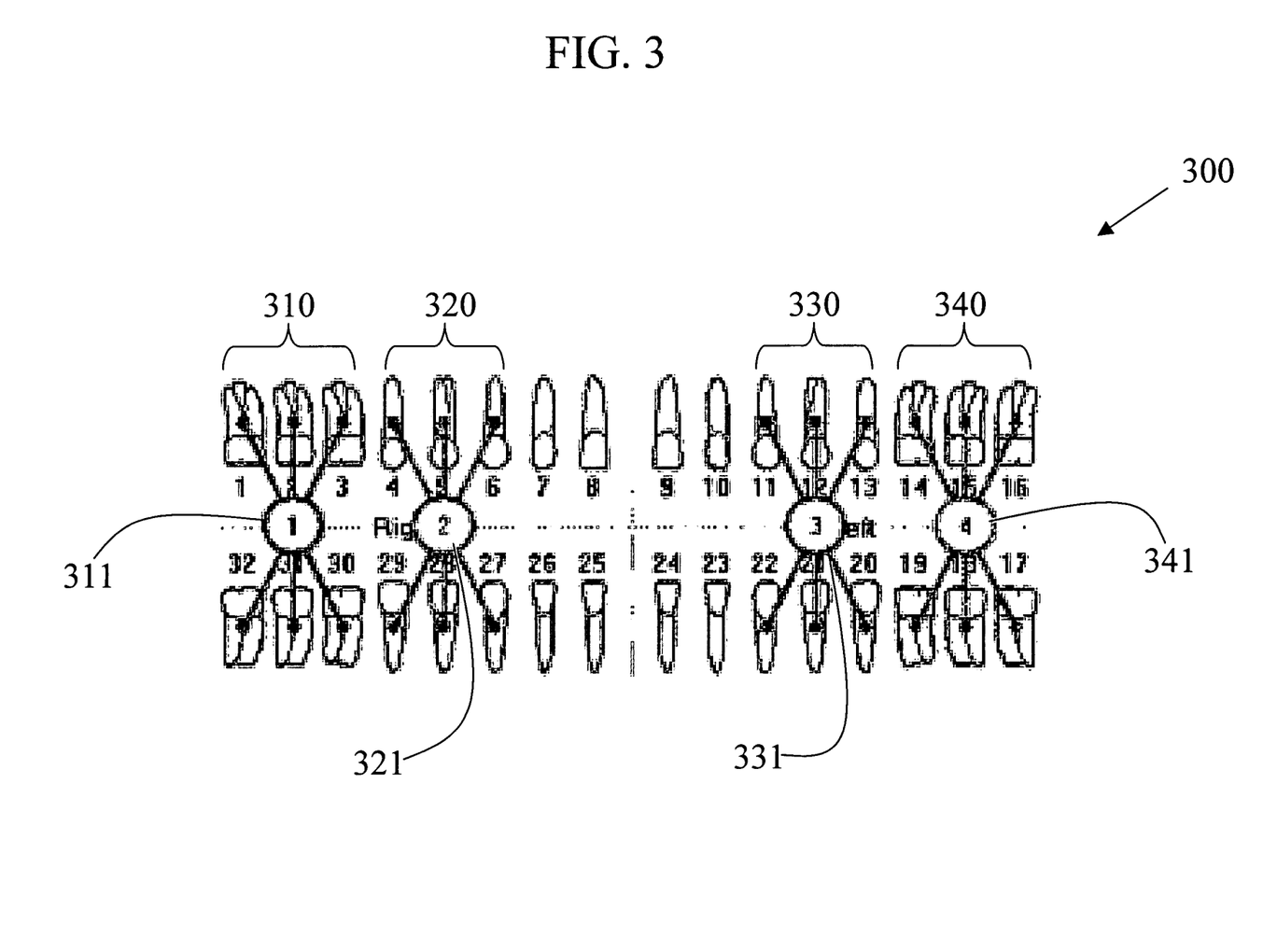
FIG. 3 illustrates an exemplary embodiment of a graphical representation of a sequence of anatomical structures generated and displayed by the system of FIG. 1 using the method of FIG. 2, in accordance with various aspects of the present invention.

FIG. 3 illustrates an exemplary embodiment of a graphical representation of a sequence of anatomical structures generated and displayed by the system 100 of FIG. 1 using the method 200 of FIG. 2, in accordance with various aspects of the present invention. The graphical representation of FIG. 3 represents a 4 Bite Wing Series of a tooth progression chart 300. The tooth progression chart 300 shows all 32 human adult teeth in correct anatomical relation to each other. Also, FIG. 3 shows a pictorial representation of a sequence or progression of four anatomical structures (i.e., four sets of teeth) 310, 320, 330, and 340 corresponding to the standard adult 4 Bite Wing Series. Each anatomical structure (310, 320, 330, 340) has associated with it a corresponding indicia (311, 321, 331, 341). Each indicia clearly indicates which teeth correspond to which anatomical structure. Note that the pictorial representations of the anatomical structures (i.e. teeth) actually look like those anatomical structures (i.e. teeth). The pictorial representations are not simply iconic symbols such as intra-oral radiograph holders.

For example, the teeth numbers 1, 2, 3, 30, 31, and 32 correspond to indicia 311. Indicia 311 includes a circled number 1 with connecting lines extending from the circled number 1 to the individual teeth (teeth numbers 1, 2, 3, 30, 31, and 32). Therefore, the six teeth (teeth numbers 1, 2, 3, 30, 31, and 32) constitute a first anatomical structure 310. The number 1 of the indicia 311 also indicates that this first anatomical structure 310 is the first anatomical structure and shot number in the defined 4 Bite Wing Series progression.

Similarly, anatomical structure 320 corresponds to the teeth numbers 4, 5, 6, 27, 28, and 29 as indicated by indicia 321 and is the second anatomical structure in the progression. Anatomical structure 330 corresponds to the teeth numbers 11, 12, 13, 20, 21, and 22 as indicated by indicia 331 and is the third anatomical structure in the progression. Anatomical structure 340 corresponds to the teeth numbers 14, 15, 16, 17, 18, and 19 as indicated by indicia 341 and is the fourth anatomical structure in the progression. Each defined anatomical structure (310, 320, 330, and 340) may have an image shot (i.e., a digital image) associated with it.

The indicia 311, 321, 331, and 341 each include a numeric character. However, in accordance with various alternative embodiments of the present invention, other representations are possible as well, including alphabetic characters (e.g., A, B, C, D) and alpha-numeric characters (e.g., 1A, 1B, 1C, 1D).

Figure 4:
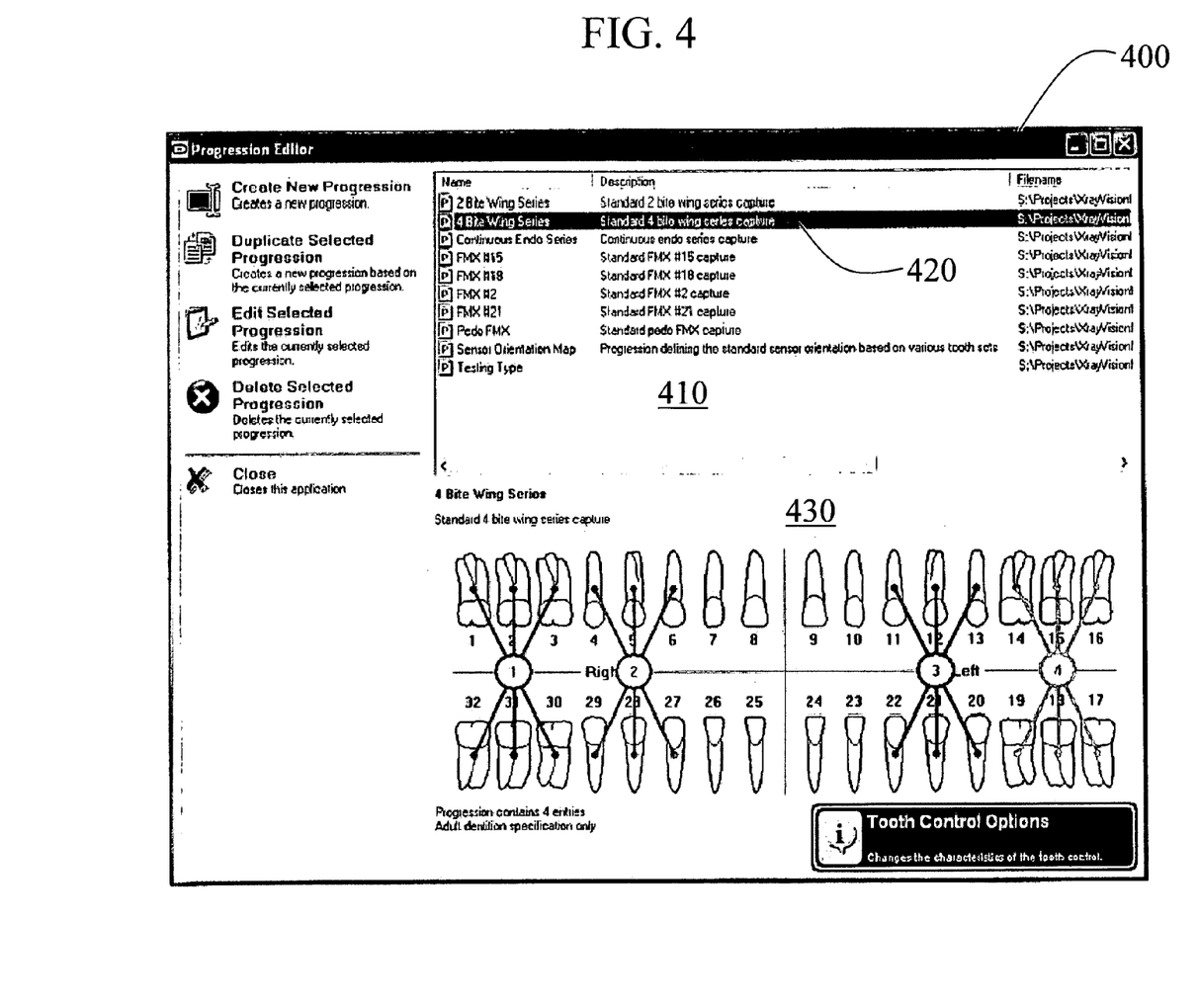
FIG. 4 illustrates an embodiment of a screen displayed by the system of FIG. 1 showing ten choices of progressions icons, in accordance with various aspects of the present invention.

FIG. 4 illustrates an embodiment of a screen 400 displayed by the system 100 of FIG. 1 showing ten choices of progressions icons, in accordance with various aspects of the present invention. The ten choices correspond to a stored list of progression series that may be called up to appear in a window 410 of the screen 400. Each progression series is defined by two or more anatomical structures and associated indicia. Each indicia defines which teeth are associated with which anatomical structure as well as the orientation of any associated image shot. The second choice 420, which is the 4 Bite Wing Series progression, is hi-lighted and displayed as a tooth progression chart 430.

Figure 5:
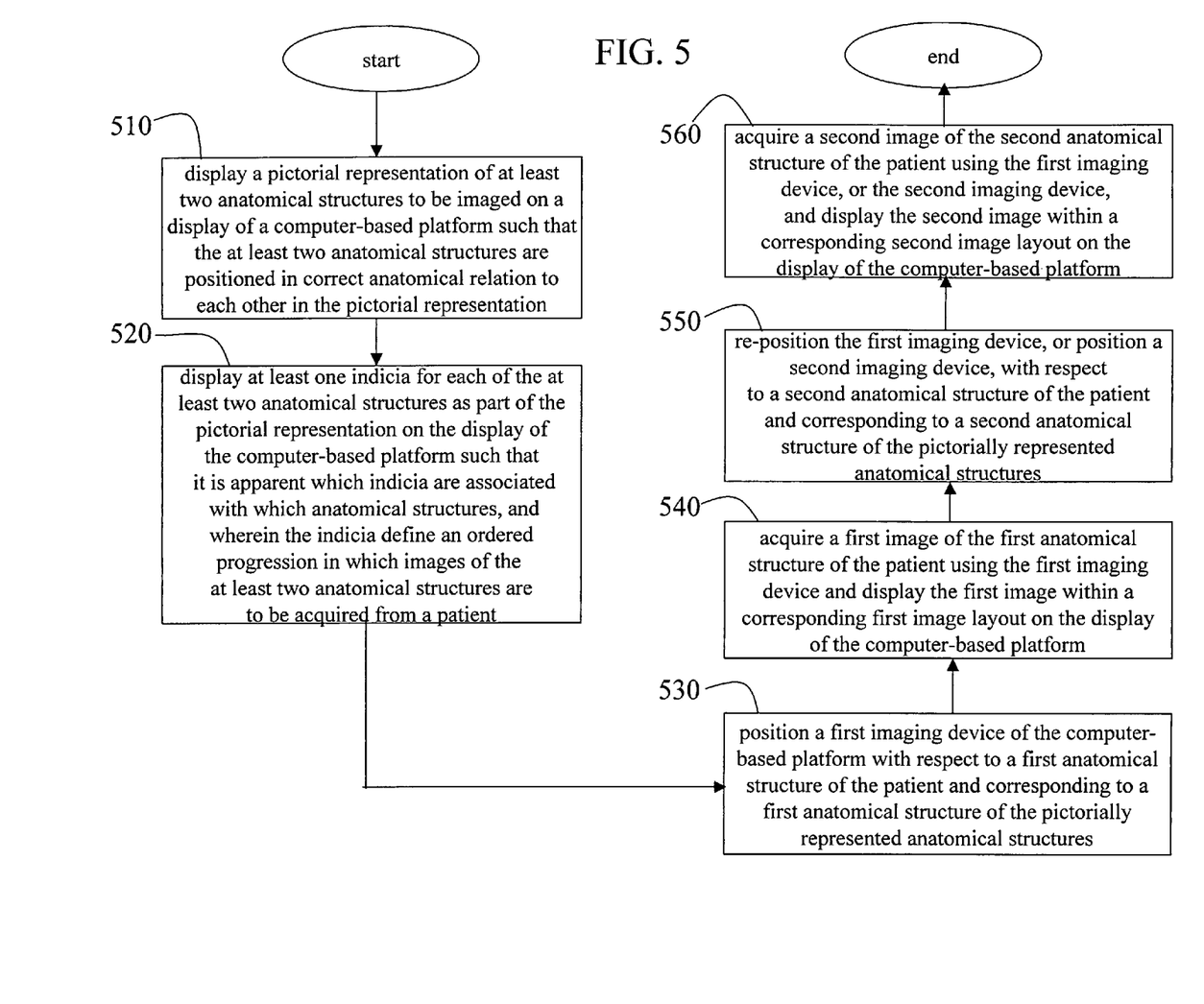
FIG. 5 illustrates a flow chart of an embodiment of a method for capturing a sequence of anatomical images using the computer-based platform of FIG. 1, in accordance with various aspects of the present invention.

FIG. 5 illustrates a flow chart of an embodiment of a method 500 for capturing a sequence of anatomical images using the computer-based platform 100 of FIG. 1, in accordance with various aspects of the present invention. In step 510, a pictorial representation of at least two anatomical structures to be imaged are displayed on a display of a computer-based platform such that the at least two anatomical structures are positioned in correct anatomical relation to each other in the pictorial representation. In step 520, at least one indicia is displayed for each of the at least two anatomical structures as a part of the pictorial representation on the display of the computer-based platform such that it is apparent which indicia are associated with which of the anatomical structures. Also, the indicia define an ordered progression in which images of the at least two anatomical structures are to be acquired from a patient. The exact order of the steps 510-520 is not necessarily critical. Other embodiments may re-order and/or combine the steps to achieve a same resultant displayed screen. In step 530, a first imaging device of the computer-based platform is positioned with respect to a first anatomical structure of the patient and corresponding to a first anatomical structure of the pictorially represented anatomical structures. In step 540, a first image of the first anatomical structure of the patient is acquired using the first imaging device and the first image is displayed within a corresponding first image layout on the display of the computer-based platform. In step 550, the first imaging device is repositioned, or a second imaging device is positioned, with respect to a second anatomical structure of the patient and corresponding to a second anatomical structure of the pictorially represented anatomical structures. In step 560, a second image of the second anatomical structure of the patient is acquired using the first imaging device, or the second imaging device, and the second image is displayed within a corresponding second image layout on the display of the computer-based platform.

Figure 6A:
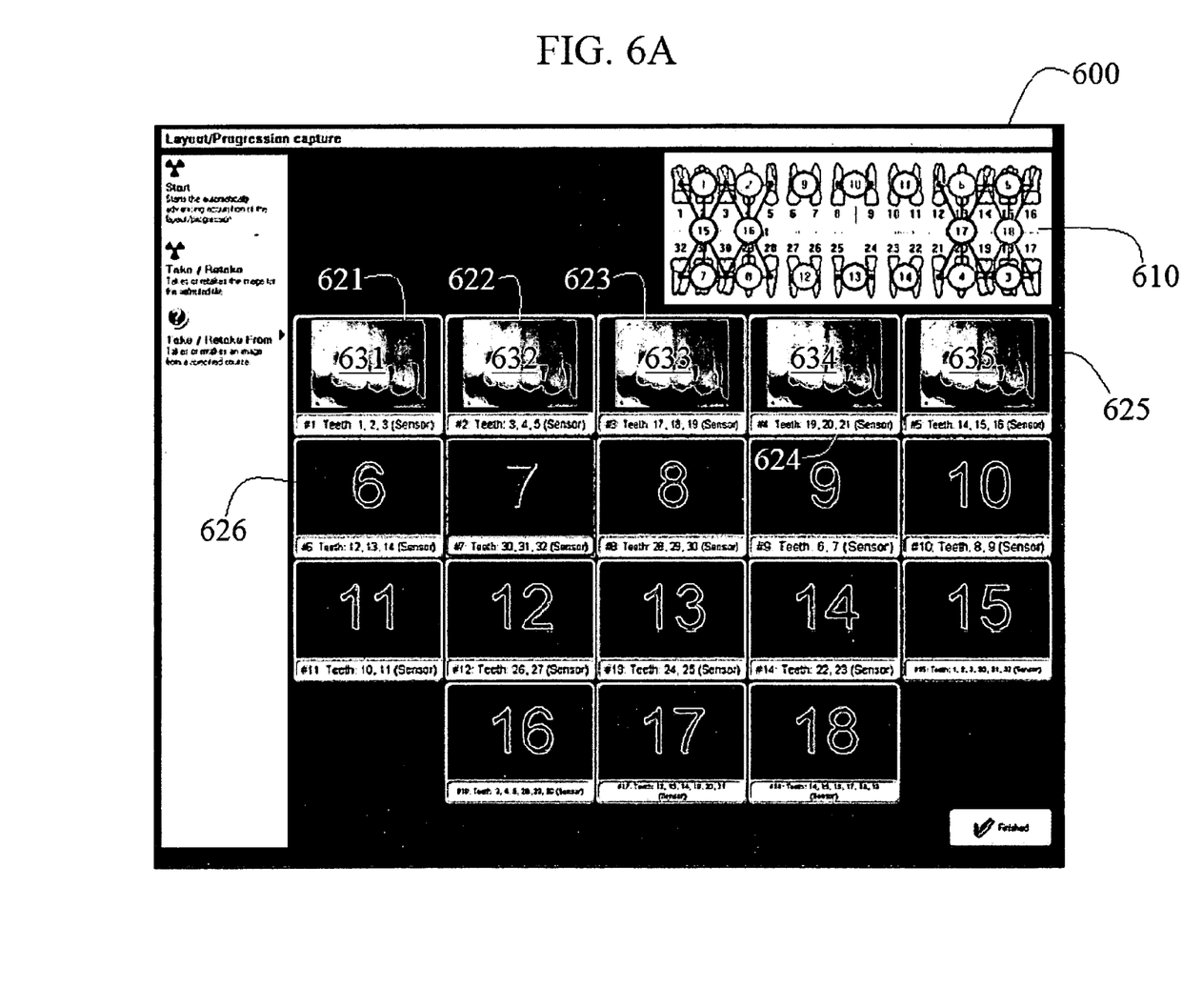
FIG. 6A illustrates an exemplary embodiment of a resultant displayed screen using the method of FIG. 5, in accordance with various aspects of the present invention.

FIG. 6A illustrates an exemplary embodiment of a resultant displayed screen 600 using the method 500 of FIG. 5, in accordance with various aspects of the present invention. The displayed screen 600 includes a tooth progression chart 610 displayed in the upper right corner for a full mouth series of eighteen images (FMX-18). The tooth progression chart 610 includes a set of numbered teeth in anatomically correct relation to each other along with corresponding indicia identifying the eighteen anatomical structures (i.e., eighteen sets of teeth) to be imaged. Displaying the tooth progression chart 610 corresponds to steps 510 and 520 of the method 500.

The vast majority of the displayed screen 600 is dedicated to displaying eighteen image layouts corresponding to the eighteen sets of teeth to be imaged in progressive order 1 to 18. For example, the first five image layouts 621-625 include captured digital images 631-635 corresponding to the first five anatomical structures in the progression as indicated by the numerical indicia in the tooth progression chart 610. In step 530 of the method 500, an imaging device (e.g., an intra-oral digital X-ray device) is positioned within the patient's mouth in order to image the first anatomical structure defined by the tooth progression chart 610. In accordance with an embodiment of the present invention, at least one of the first image layout, the first anatomical structure, and the indicia associated with the first anatomical structure is automatically high-lighted on the display of the computer-based platform when the first image is to be acquired. According to step 540 in the method 500, the first image 631 is acquired and displayed in the first image layout 621. This first image 631 and first image layout 621 correspond to the first anatomical structure defined in the tooth progression chart 610 which corresponds to the teeth numbers 1, 2, and 3.

According to step 550 of the method 500, the imaging device is re-positioned within the patient's mouth in order to image the second anatomical structure defined by the tooth progression chart 610, or a second imaging device may be used. In accordance with an embodiment of the present invention, at least one of the second image layout, the second anatomical structure, and the indicia associated with the second anatomical structure is automatically high-lighted on the display after the first image has been acquired and when the second image is to be acquired. Subsequently, according to step 560 of the method 500, the second image 632 is acquired and displayed in the second image layout 622. This second image 632 and second image layout 622 correspond to the second anatomical structure defined in the tooth progression chart 610 which corresponds to the teeth numbers 3, 4, and 5. As shown in FIG. 6A, the method has been continued to acquire and display three more images 633-635 of the next three anatomical structures defined by the tooth progression chart 610 in their corresponding image layouts 623-625. The method may continue until all eighteen anatomical structures (i.e., predefined sets of teeth) are captured for the FMX-18 series.

Figure 6B:
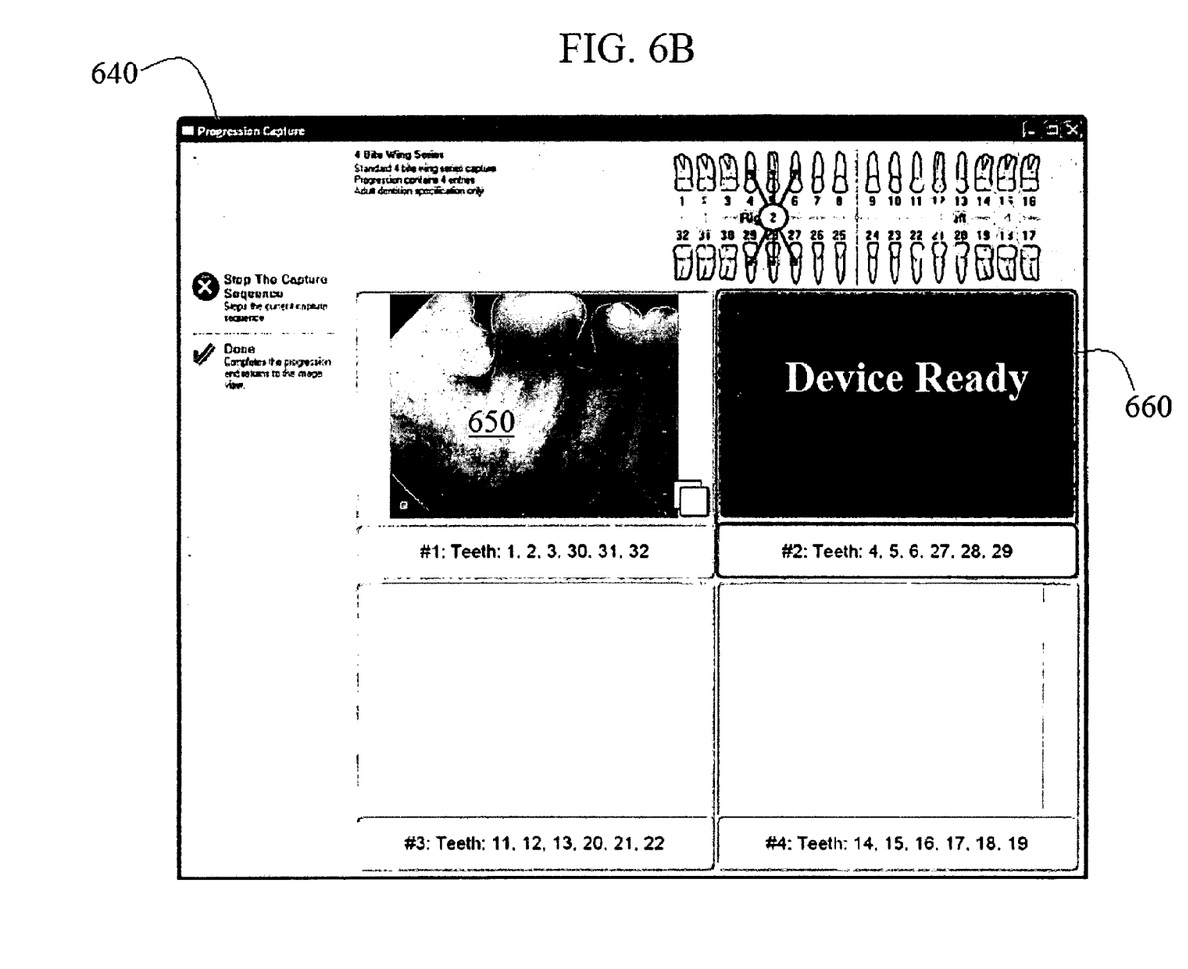
FIG. 6B illustrates an exemplary embodiment of a resultant displayed screen after having captured a first image and when preparing to capture a second image in a second image layout, in accordance with various aspects of the present invention.

Also, various status messages may be displayed in the current image layout. For example, FIG. 6B illustrates an exemplary embodiment of a resultant displayed screen 640 after having captured a first image 650 and when preparing to capture a second image in image layout 660, in accordance with various aspects of the present invention. The status message "Device Ready" is displayed in the image layout 660, indicating to the user that the system is ready to capture the next image. Other status messages are possible as well, in accordance with various embodiments of the present invention.

In accordance with various embodiments of the present invention, a first imaging device of a first type (e.g., a digital X-ray device) may be used to generate and store a first digital image as a first image shot in a progression of image shots, and a second imaging device of a second type (e.g., a digital camera or a digital video camera) may be used to generate and store a second digital image as a second image shot in the same progression of image shots. That is, in general, different image shots within a progression of image shots may correspond to digital images generated using different imaging devices. This brings more flexibility to the user when performing exams or studies.

If a dentist makes a mistake by imaging a wrong anatomical structure (i.e., an anatomical structure that does not correspond to the current image layout with which the image will be associated and displayed), then the dentist can delete the image or move the image. For example, referring to FIG. 6A, if the image 635 really corresponds to teeth numbers 12, 13, and 14 (i.e., image layout 626), then the dentist can use the user interface 130 to select the image 635 and drag it from image layout 625 into image layout 626. Alternatively, the dentist may use the user interface 130 to delete the image 635. Then the dentist may re-position the imaging device and recapture an image for the image layout 625. In general, a user may move any image from one image layout to another, or may delete any image within an image layout. Also, a user may drag multiple images to a "drop area" or a temporary holding location, and then re-order the images in the image layouts. Furthermore, a user may view all of the images, which may not yet be assigned to any image layout, and then select an image to go into a selected image layout. Other methods of arranging and assigning images are possible as well, in accordance with various embodiments of the present invention.

Figure 7:
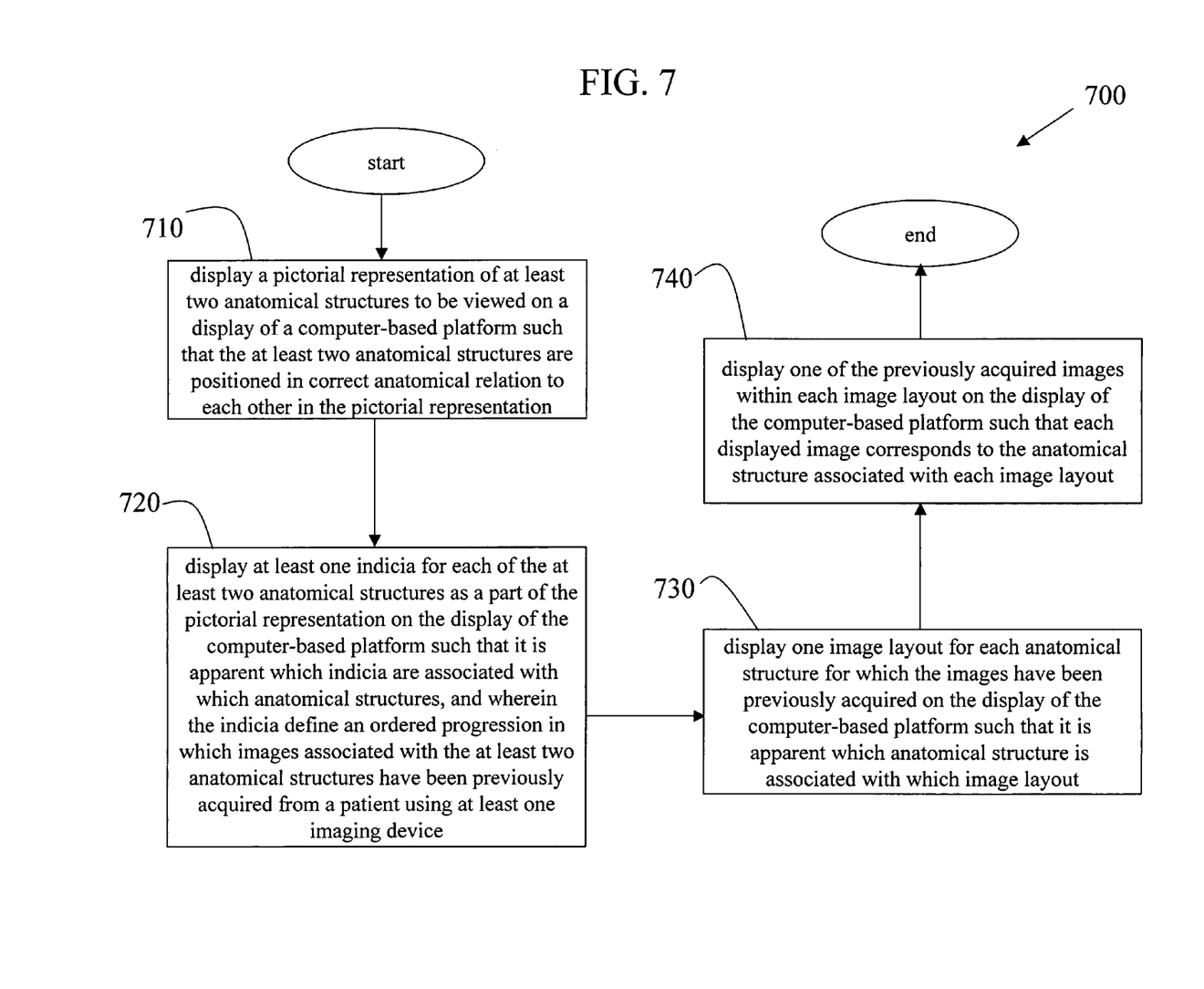
FIG. 7 illustrates a flow chart of an embodiment of a method for viewing a sequence of previously captured anatomical images on the computer-based platform of FIG. 1, in accordance with various aspects of the present invention.

FIG. 7 illustrates a flow chart of an embodiment of a method 700 for viewing a sequence of previously captured anatomical images on the computer-based platform 100 of FIG. 1, in accordance with various aspects of the present invention. In step 710, a pictorial representation of at least two anatomical structures to be viewed on a display of a computer-based platform are displayed such that the at least two anatomical structures are positioned in correct anatomical relation to each other in the pictorial representation. In step 720, at least one indicia for each of the at least two anatomical structures is displayed as part of the pictorial representation on the display of the computer-based platform such that it is apparent which indicia are associated with which anatomical structures. The indicia define an ordered progression in which images associated with the at least two anatomical structures have been previously acquired from a patient using at least one imaging device. In step 730, one image layout for each anatomical structure for which the images have been previously acquired is displayed on the display of the computer-based platform such that it is apparent which anatomical structure is associated with which image layout. In step 740, one of the previously acquired images is displayed within each image layout on the display of the computer-based platform such that each displayed image corresponds to the anatomical structure associated with each image layout. The exact order of the steps 710-740 is not necessarily critical. Other embodiments may re-order and/or combine the steps to achieve a same resultant displayed screen.

Figure 8:
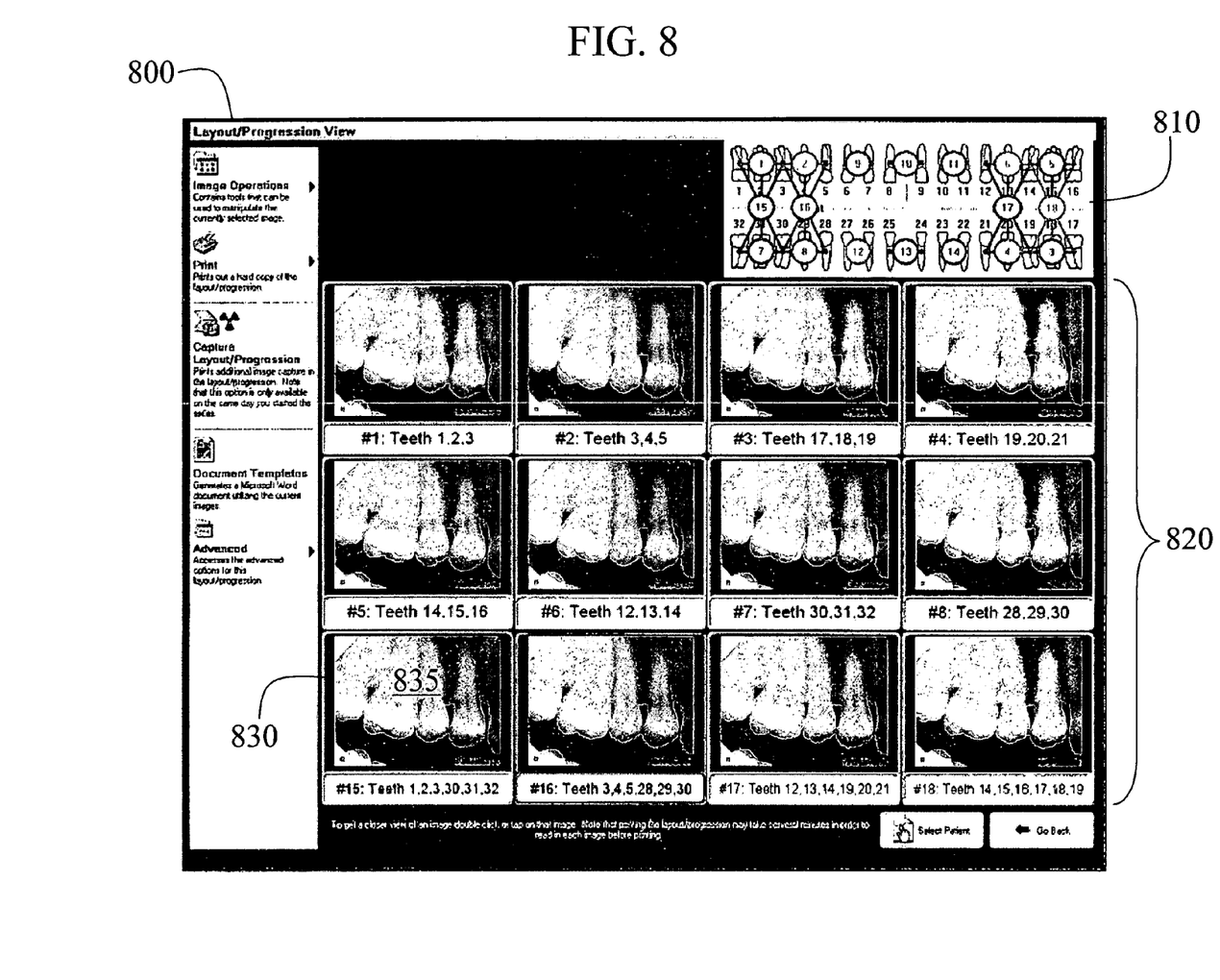
FIG. 8 illustrates an exemplary embodiment of a resultant displayed screen using the method of FIG. 7, in accordance with various aspects of the present invention.

FIG. 8 illustrates an exemplary embodiment of a resultant displayed screen 800 using the method 700 of FIG. 7, in accordance with various aspects of the present invention. The displayed screen 800 includes a tooth progression chart 810 displayed in the upper right corner for a full mouth series of eighteen images (FMX-18). The tooth progression chart 810 includes a set of numbered human teeth in anatomically correct relation to each other along with corresponding indicia identifying the eighteen anatomical structures (i.e., eighteen sets of teeth) to be viewed. Displaying the tooth progression chart 810 corresponds to steps 710 and 720 of the method 700. Notice that any given tooth may be associated with more than one anatomical structure and, therefore, with more than one indicia. For example, tooth number 1 is associated with indicia 1 and indicia 15 (i.e., anatomical structure 1 which includes teeth numbers 1, 2, and 3; and anatomical structure 15 which includes teeth numbers, 1, 2, 3, 30, 31, and 32).

The vast majority of the displayed screen 800 is dedicated to displaying those image layouts with images that have been previously captured. Displaying the image layouts that have corresponding images corresponds to steps 730 and 740 of the method 700. In the displayed screen 800, only twelve image layouts 820, of eighteen possible image layouts, and corresponding twelve images are displayed. The twelve image layouts 820 correspond to twelve of the eighteen anatomical structures in the tooth progression chart 810. In this example, only twelve images were previously captured and stored. Therefore, only twelve images are displayed in the twelve image layouts. For example, the dentist may have had a reason to only capture the images of these twelve anatomical structures and not the other six. Or the dentist may have recently deleted the other six images. In either case, the image layouts 820 and corresponding images are displayed in progression order (1-18) even though progressions 9-14 are not displayed since there are no corresponding images.

In accordance with an embodiment of the present invention, the displayed size of each of the twelve image layouts and corresponding images is adapted to make maximum use of the display screen. For example, if all eighteen image layouts contained images, then all eighteen image layouts would be displayed on the display screen but each image layout would be adapted to be smaller in size to make room for the extra six image layouts to be displayed. Similarly, if fewer than twelve images were available, then the displayed size would be increased for each image layout and corresponding image. In general, the display size of any image layout and associated image is inversely proportional to the number of images to be displayed.

In accordance with an alternative embodiment of the present invention, only one image layout is displayed at a time on the display 160 and the user may use the user interface 130 to scroll through the various image layouts and associated images on the display 160. As a result, the displayed size of each image layout may be fairly large.

Also, a user may use the user interface 130 to select a single image to be displayed from the set of currently displayed image layouts 820. For example, a user (e.g., dentist) may click on image 835 of image layout 830. The image 835 would be increased in size on the display. The other images would not be displayed. Alternatively, the user may click on the corresponding anatomical structure or indicia on the tooth progression chart 810 in order to display a single image. In general, a user may select any number of images to display out of the full set of images available in the progression set or may scroll through the images.

Figure 9:
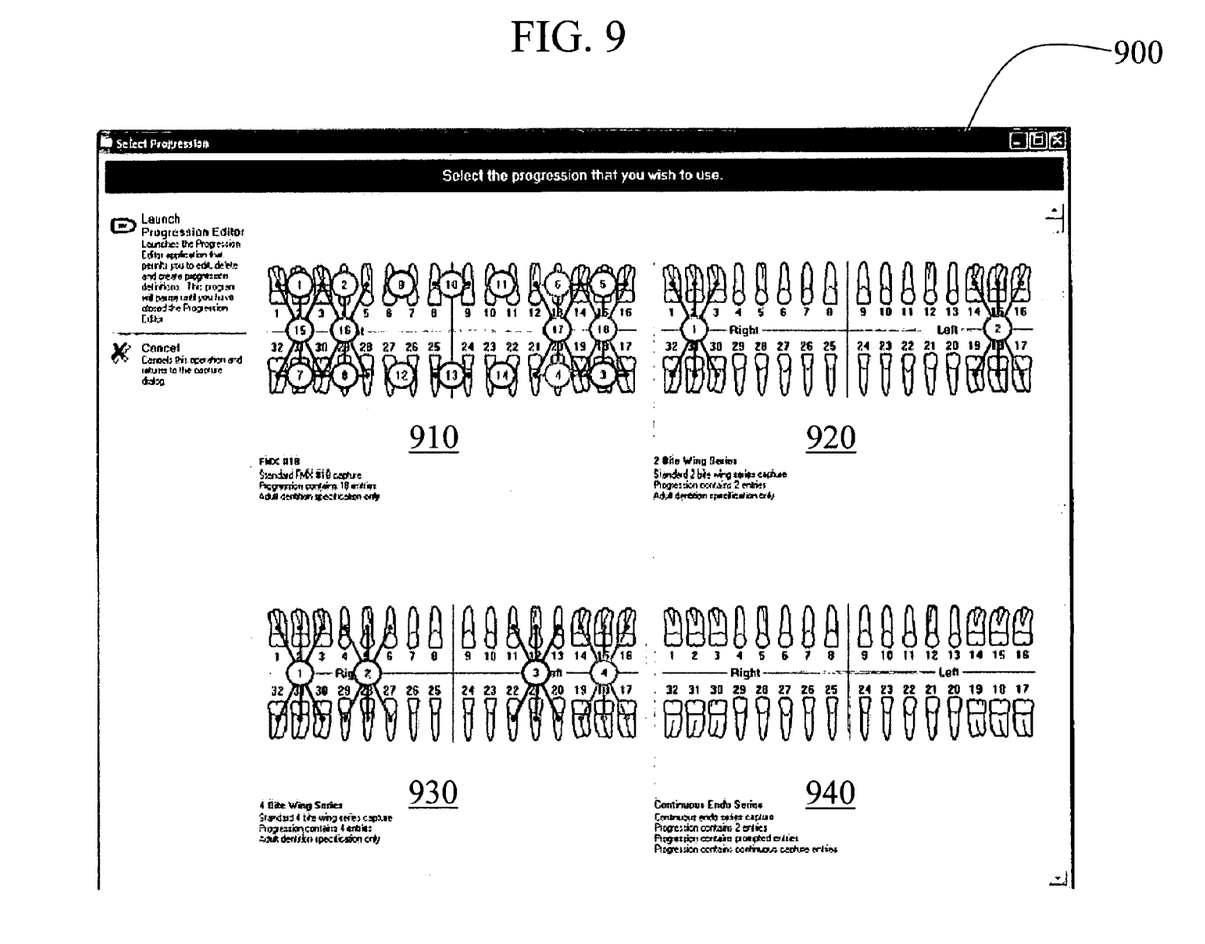
FIG. 9 illustrates an exemplary embodiment of a displayed screen displayed by the system of FIG. 1 showing four choices of progression series in an alternative format to that of FIG. 4, in accordance with various aspects of the present invention.

FIG. 9 illustrates an exemplary embodiment of a displayed screen 900 displayed by the system 100 of FIG. 1 showing four choices of progression series 910, 920, 930, and 940 in an alternative format to that of FIG. 4, in accordance with various aspects of the present invention. The four progression series 910-940 are each displayed as a tooth progression chart in the displayed screen 900. In accordance with an embodiment of the present invention, representations of the progression series (i.e., the tooth progression charts) are displayed in the most-recently used order and are selected by clicking on the respective representation. The first progression series 910 corresponds to a standard FMX series, the second progression series 920 corresponds to a standard 2 bite wing series, the third progression series 930 corresponds to a standard 4 bite wing series, and the fourth progression series 940 corresponds to a continuous endo series. Many other standard and custom series are possible as well in accordance with various embodiments of the present invention.

In accordance with various embodiments of the present invention, mixed dentition may be specified for each image shot within a progression of image shots. A user may also specify an orientation (e.g., left, right) of any of the images to be acquired in a progression using the user interface of the computer-based platform system. The specified orientation is displayed as a part of at least one of the pictorial representation (as shown in FIG. 4) or the associated image layout. Also, the system and methods described herein may be adapted to other forms of medical imaging besides that of dentistry. For example, instead of using a tooth chart, the system and methods may use some other anatomical type of chart (e.g., a chart showing various anatomical structures within a patient's hand).

In summary, embodiments of the present invention provide a system and methods for capturing, displaying, and viewing representations of progressions of anatomical structures and associated digital images. The methods and system allow a user to work more efficiently when performing exams or studies of regions of interest.

While the invention has been described with reference to certain embodiments, it will be understood by those skilled in the art that various changes may be made and equivalents may be substituted without departing from the scope of the invention. In addition, many modifications may be made to adapt a particular situation or material to the teachings of the invention without departing from its scope. Therefore, it is intended that the invention not be limited to the particular embodiments disclosed, but that the invention will include all embodiments falling within the scope of the appended claims.

What is claimed is:

1. A method of graphically representing a sequence of anatomical structures to be imaged or which have been imaged in a pre-defined ordered progression, said method comprising:
displaying a pictorial representation of at least two anatomical structures such that said at least two anatomical structures are positioned in correct anatomical relation to each other in said pictorial representation; and
displaying at least one indicia for each of said at least two anatomical structures as a part of said pictorial representation such that it is apparent which said indicia are associated with which said anatomical structures, and wherein said indicia define an ordered progression in which said at least two anatomical structures are to be imaged or have been imaged.

2. The method of claim 1 wherein each of said at least two anatomical structures comprises at least one tooth of a human being.

3. The method of claim 1 wherein said indicia comprise at least one of numerical representations, alphabetic representations, and alpha-numeric representations.

4. A method of capturing a sequence of anatomical images in a pre-defined ordered progression using a computer-based platform, said method comprising:
displaying a pictorial representation of at least two anatomical structures to be imaged on a display of said computer-based platform such that said at least two anatomical structures are positioned in correct anatomical relation to each other in said pictorial representation;
displaying at least one indicia for each of said at least two anatomical structures as a part of said pictorial representation on said display of said computer-based platform such that it is apparent which said indicia are associated with which said anatomical structures, and wherein said indicia define an ordered progression in which images of said at least two anatomical structures are to be acquired from a patient;
positioning a first imaging device of said computer-based platform with respect to a first anatomical structure of said patient and corresponding to a first anatomical structure of said pictorially represented anatomical structures as indicated by said associated indicia;
acquiring a first image of said first anatomical structure of said patient using said first imaging device and displaying said first image within a corresponding first image layout on said display of said computer-based platform;
repositioning said first imaging device, or positioning a second imaging device, with respect to a second anatomical structure of said patient and corresponding to a second anatomical structure of said pictorially represented anatomical structures as indicated by said associated indicia; and acquiring a second image of said second anatomical structure of said patient using said first imaging device, or said second imaging device, and displaying said second image within a corresponding second image layout on said display of said computer-based platform.

5. The method of claim 4 wherein at least one of said first image layout, said first anatomical structure, and said indicia associated with said first anatomical structure is automatically high-lighted on said display of said computer-based platform when said first image is to be acquired.

6. The method of claim 5 wherein at least one of said second image layout, said second anatomical structure, and said indicia associated with said second anatomical structure is automatically high-lighted on said display after said first image has been acquired and when said second image is to be acquired.

7. The method of claim 4, further comprising:
repositioning said first imaging device, or said second imaging device, with respect to a third anatomical structure of said patient and corresponding to a third anatomical structure of said pictorially represented anatomical structures as indicated by said associated indicia; and
acquiring a third image of said third anatomical structure of said patient using said first imaging device, or said second imaging device, and displaying said third image within a corresponding third image layout on said display of said computer-based platform.

8. The method of claim 4, further comprising:
positioning a third imaging device of said computer-based platform with respect to a third anatomical structure of said patient and corresponding to a third anatomical structure of said pictorially represented anatomical structures as indicated by said associated indicia; and
acquiring a third image of said third anatomical structure of said patient using said third imaging device and displaying said third image within a corresponding third image layout on said display of said computer-based platform.

9. The method of claim 7 wherein each of said at least two anatomical structures comprises at least one tooth of a human being.

10. The method of claim 7 wherein said indicia comprise at least one of numerical representations, alphabetic representations, and alpha-numeric representations.

11. The method of claim 7 wherein said first imaging device and said second imaging device each comprise one of a digital X-ray device, a digital camera, and a digital video camera.

12. The method of claim 8 wherein each of said at least two anatomical structures comprises at least one tooth of a human being.

13. The method of claim 8 wherein said indicia comprise at least one of numerical representations, alphabetic representations, and alpha-numeric representations.

14. The method of claim 8 wherein each of said first, second, and third imaging devices comprises one of a digital X-ray device, a digital camera, and a digital video camera.

15. The method of claim 4 further comprising re-associating said first image with said second image layout and said second anatomical structure by selecting said first image on said display and dragging said first image from said first image layout into said second image layout using a user interface of said computer-based platform.

16. The method of claim 7 further comprising re-associating said first image with said third image layout and said third anatomical structure by selecting said first image on said display and dragging said first image from said first image layout into said third image layout using a user interface of said computer-based platform.

17. The method of claim 7 further comprising re-associating said second image with said third image layout and said third anatomical structure by selecting said second image on said display and dragging said second image from said second image layout into said third image layout using a user interface of said computer-based platform.

18. The method of claim 4 further comprising specifying an orientation of at least one of said first image and said second image, using a user interface of said computer-based platform, such that said specified orientation is displayed as a part of at least one of said pictorial representation and said corresponding image layout.

19. A method of viewing a sequence of anatomical images, previously captured in an ordered progression, on a computer-based platform, said method comprising:
displaying a pictorial representation of at least two anatomical structures to be viewed on a display of said computer-based platform such that said at least two anatomical structures are positioned in correct anatomical relation to each other in said pictorial representation;
displaying at least one indicia for each of said at least two anatomical structures as a part of said pictorial representation on said display of said computer-based platform such that it is apparent which said indicia are associated with which said anatomical structures, and wherein said indicia define an ordered progression in which images associated with said at least two anatomical structures have been previously acquired from a patient using at least one imaging device;
displaying one image layout for each said anatomical structure for which said images have been previously acquired on said display of said computer-based platform such that it is apparent which said anatomical structure is associated with which said image layout; and
displaying one of said previously acquired images within each said image layout on said display of said computer-based platform such that each displayed image corresponds to said anatomical structure associated with each said image layout.

20. The method of claim 19 wherein each of said at least two anatomical structures comprises at least one tooth of a human being.

21. The method of claim 19 wherein said indicia comprise at least one of numerical representations, alphabetic representations, and alpha-numeric representations.

22. The method of claim 19 wherein said at least one imaging device comprises at least one of a digital X-ray device, a digital camera, and a digital video camera.

23. The method of claim 19 wherein a display size of each said image layout is inversely proportional to a number of said images to be displayed.

24. The method of claim 19 further comprising displaying only one image of said images on said display of said computer-based platform by selecting said one image using a user interface of said computer-based platform.

25. The method of claim 19 further comprising viewing only one image of said images at a time on said display of said computer-based platform by scrolling through said images using a user interface of said computer-based platform.

26. A computer-based system for capturing and displaying progressions of anatomical images, said system comprising:
a display;
means for generating and displaying, on said display, a pictorial representation of at least two anatomical structures to be imaged and associated indicia, and wherein said associated indicia define an ordered progression in which images of said at least two anatomical structures are to be acquired or have been acquired from a patient;

at least one imaging device for generating at least two digital images of said at least two anatomical structures of said patient corresponding to said displayed pictorial representation of said least two anatomical structures;

a memory to store said at least two digital images; and means for generating and displaying, on said display, one image layout for each of said at least two digital images such that it is apparent which said anatomical structure is associated with which said image layout, and wherein said at least two digital images are displayed within said image layouts on said display in proper correspondence to said at least two anatomical structures.

27. The computer-based system of claim 26 wherein said at least one imaging device comprises at least one of a digital X-ray device, a digital camera, and a digital video camera.

28. The computer-based system of claim 26 wherein each of said at least two anatomical structures comprises at least one tooth of a human being.

29. The computer-based system of claim 26 wherein said indicia comprise at least one of numerical representations, alphabetic representations, and alpha-numeric representations.

30. The computer-based system of claim 26 further comprising a user interface allowing a user of said system to control said system.

* * * * *